Figure 1:
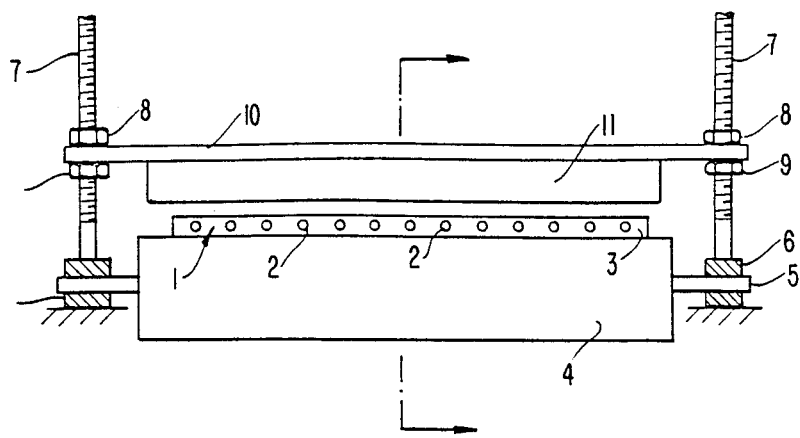

United States Patent [19]
Harrison

[11] Patent Number: 4,864,233
[45] Date of Patent: Sep. 5, 1989

[54] MAGNETIC DETECTION OF AIR GAPS FORMED AT BREAKS IN CONVEYOR BELT CARDS

[75] Inventor: Alexander Harrison, Beecroft, Australia

[73] Assignee: Commonwealth Scientific and Industrial Research Organisation, Australia

[21] Appl. No.: 761,971

[22] Filed: Aug. 1, 1985

[30] Foreign Application Priority Data

Aug. 3, 1984 [AU] Australia ............................ PG6384

[51] Int. Cl.⁴ ...................... G01N 27/72; G01N 27/82; G01R 33/12
[52] U.S. Cl. .................................. 324/227; 324/232; 324/240
[58] Field of Search ............... 324/226, 227, 232, 239, 324/240, 243; 361/143, 149

[56] References Cited

U.S. PATENT DOCUMENTS

| | | | |
|---|---|---|---|
| 2,677,802 | 5/1954 | Irwin | 324/232 |
| 3,271,664 | 9/1966 | Mountz et al. | 324/227 |
| 4,439,731 | 3/1984 | Harrison | 324/243 |

FOREIGN PATENT DOCUMENTS 584239  12/1977  U.S.S.R. .............................. 324/234

Primary Examiner—Reinhard J. Eisenzopf
Assistant Examiner—Walter E. Snow
Attorney, Agent, or Firm—Lyon & Lyon

[57] ABSTRACT

There is disclosed herein a method and apparatus wherein conveyor belt cords are first de-gaussed to remove any stray magnetic fields, and then longitudinal unidirectionally magnetized. The belt is then magnetically scanned and the electrical output signal is passed through a low pass filter in order to produce a break signal indicative of breaks in the magnetically permeable cords of the conveyor belt.

5 Claims, 4 Drawing Sheets

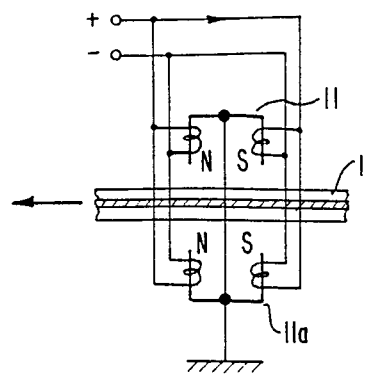
*FIG. 4.*
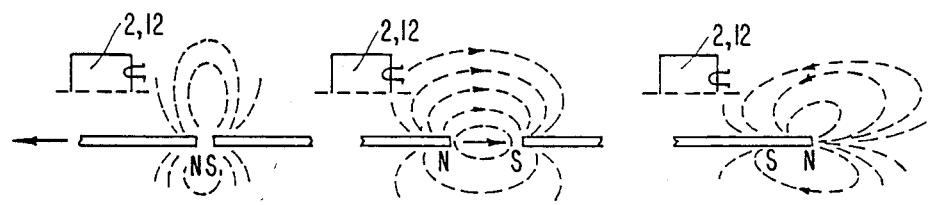
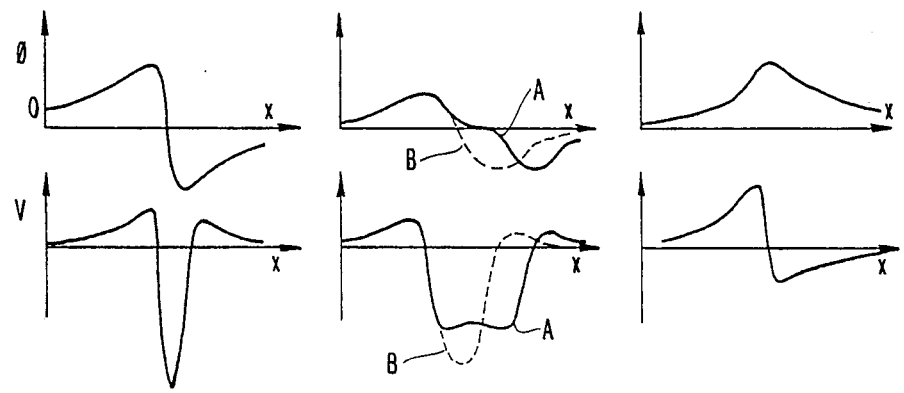
*FIG. 5a.*  *FIG. 5b.*  *FIG. 5c.*

MAGNETIC DETECTION OF AIR GAPS FORMED AT BREAKS IN CONVEYOR BELT CARDS

The present invention relates to a method and apparatus for detecting breaks in the steel cords of conveyor belts but is generally applicable to detecting the breaks in elongate magnetically permeable members which are embedded in a non-magnetically permeable material.

Australian Pat. No. 535,356 (to which U.S. Pat. No. 4,439,731 corresponds) discloses a method and apparatus for detecting the corrosion, and hence loss of magnetically permeable material, from conveyor belt cords. However, the method and apparatus disclosed in the abovementioned patent are of no assistance in locating breaks in such cords, especially where the break does not constitute an extended gap and therefore the ends of the cord may well be abutting save for a very small air gap. Thus in a reluctance circuit where the air gap between the cord and the magnetic yoke carrying field and sensing windings may be very much greater than the air gap formed by the break in the cords, such breaks are unable to be detected.

Clearly, since such breaks weaken the mechanical strength of the conveyor belt, it is highly desirable to detect the presence of such breaks in order to permit the repair of same or the cutting of the defect section from the belt and its replacement with a new section before the belt mechanically fails in use.

Accordingly, it is an object of the present invention to provide a method and apparatus whereby such breaks can be detected.

It is known in the testing of steel haulage cable such as is used in mines to raise and lower loads up and down a shaft, to pass the steel cable through a DC current carrying solenoid which has a search coil or solenoid co-axially arranged therewith. Thus the cable also passes through the search solenoid. The passage of the cable through the current carrying solenoid longitudinally magnetises the cable. In the event that there are any breaks in the steel strands which form the cable, such breaks create a fringing magnetic field which extends beyond the cable and which is able to be detected by the search solenoid as the cable passes. The break simply records as a pulse of voltage or current in the coil which permits the cable to be stopped and inspected.

However, this technique suffers from a number of disadvantages, not the least of which is that the steel cable may contain residual magnetization brought about by its proximity to electric cables carrying welding currents, and similar sources of stray magnetizing fields. In addition, the technique is highly specialised since only effectively a single cable is involved. Thus it is a relatively easy matter to detect all of the small fringing field by means of the annular search coil which surrounds the cable. Furthermore, since the cable is not covered with a layer of material such as rubber, the search coil can be located close to the cable. Accordingly, there are a number of substantial differences between this art and the requirements of conveyor belts, in particular.

According to one aspect of the present invention there is disclosed a method of detecting breaks in elongate magnetically permeable members embedded in a non-magnetically permeable material, said method comprising the steps of:

1. Substantially reducing or eliminating any stray or residual magnetic fields in said members,
2. Longitudinally magnetizing said members with a substantially unidirectional magnetic field, thereby causing a fringing field at the location of an air gap at any break or breaks in said members,
3. Causing relative movement between said material and a field winding means to induce a time varying longitudially extending magnetic field in said members,
4. Causing relative movement between said material and a sensing winding means to generate an electric signal indicative of a total magnetic field in said members, and
5. Passing said electric signal through a low pass filter to generate an output indicative of the location of said break or breaks.

According to another aspect of the present invention there is disclosed apparatus for detecting breaks in elongate magnetically permeable members embedded in a non-magnetically permeable material, said apparatus comprising de-gaussing means to substantially eliminate any stray magnetic fields in said members, a magnetic field means movable relative to said members to create a longitudinally extending undirectional magnetic field in said members, a field winding means extending substantially transversely to said members and movable relative thereto, a sensing winding means extending substantially transversely to said members and movable relative thereto, an AC signal generator connected to said field winding means and a low pass filter connected to said sensing winding means.

Figure 2:
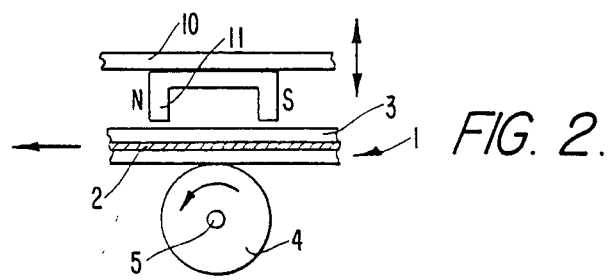
Figure 3:
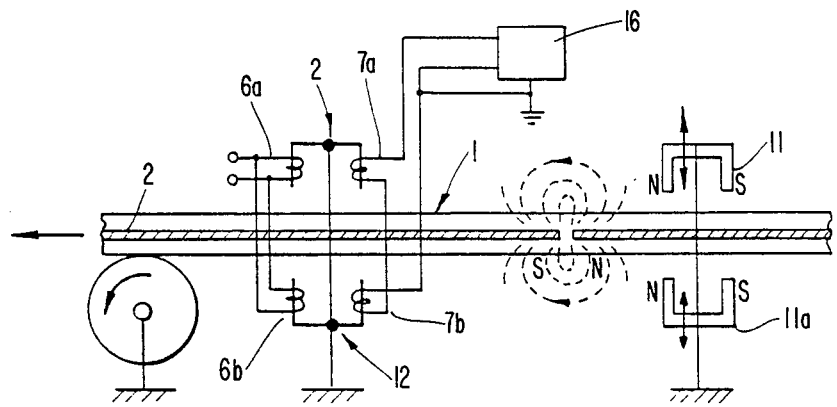
Figure 6:
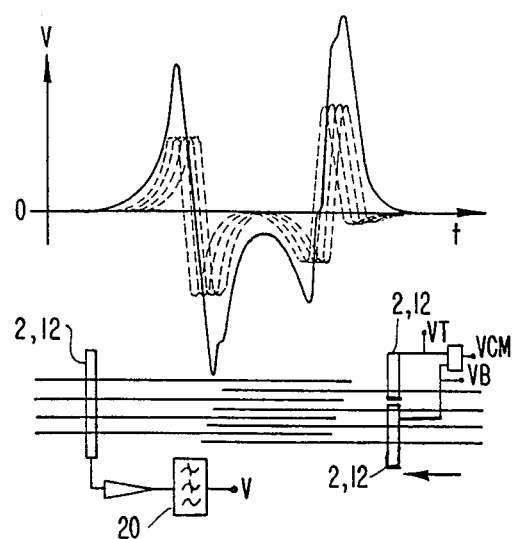
Figure 7:
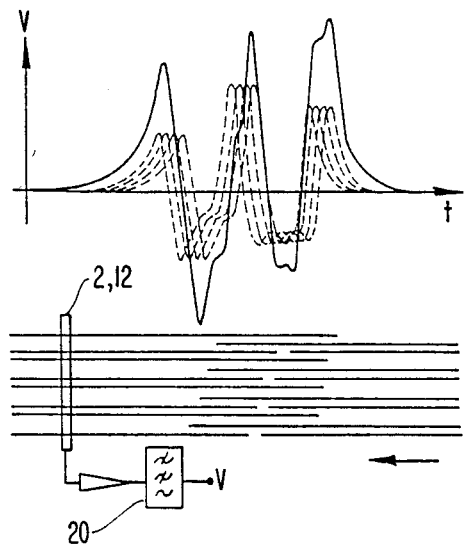
Figure 8:
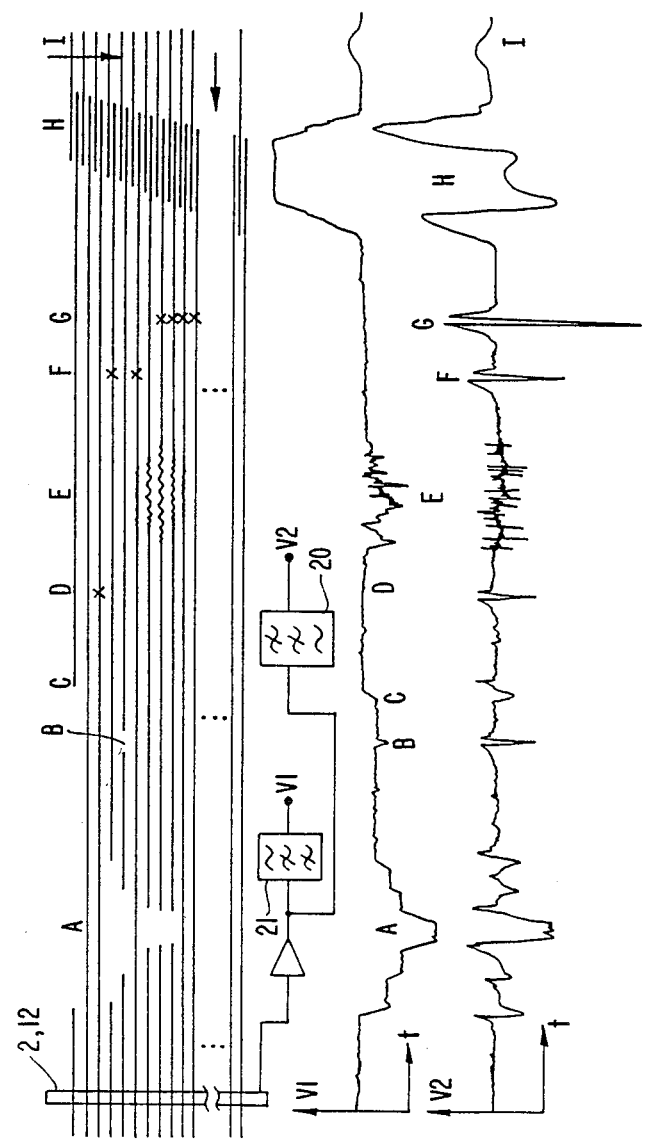

One embodiment of the present invention will now be described with reference to both the disclosure of Australian Pat. No. 535,356 (or U.S. Pat. No. 4,439,731) which is hereby incorporated herein, and also the accompanying drawings in which:

FIG. 1 is a transverse cross sectional view of a conveyor belt which is passing over an idler roller and underneath a magnet, FIG. 2 is a cross sectional view along the line II-II of FIG. 1, FIG. 3 is a view similar to that of FIG. 2 but showing a permanent magnet supporting arrangement, FIG. 4 shows a modification of the arrangement of FIG. 3 with electromagnets for aboveground use, FIGS. 5(a), 5(b) and 5(c) respectively schematically indicate cord conditions, flux conditions and voltage waveforms for a touching cord break, a cord gap, and a cord end, FIG. 6 is a graph of the voltage output as in FIG. 5 but for a Type I splice, the cord arrangement of the splice also being illustrated, FIG. 7 is a graph and cord arrangement as for FIG. 6 but for a Type 2 splice, and FIG. 8 is a schematic representation of a conveyor belt showing various cord defects and the corresponding corrosion signature and break data voltage output.

One method of failure of conveyor belts is through the fracture or breaking of its steel reinforcing cords as a result mainly of impact loads caused by the material to be conveyed falling downwardly onto the belt from a loading hopper, chute, or the like. The longitudinally extending magnetically permeable steel cords of the conveyor belt are embedded in a rubber or other elastomeric coating and thus the belt is mechanically similar to other reinforced bodies containing high tensile load bearing permeable members which are embedded in a non magnetic material.

The magnetically permeable cords of the belt are readily permanently magnetized by any stray magnetic fields such as magnetized tools, welding leads which may be draped across the belt, and other sources of transient magnetic fields that result from current switching, for example.

It has been experimentally determined that in order to provide a first step in detecting the presence of such breaks, it is necessary to first magnetically pre-condition the belt in order to remove such spurious magnetic fields. This pre-conditioning can be achieved in accordance with the apparatus illustrated in FIGS. 1 and 2 in which a conveyor belt 1 having magnetic cords 2 embedded in rubber 3 passes over an idler roller or drum 4. The drum 4 is supported by an axle 5 which is mounted in a pair of journals or bearings 6.

A threaded rod 7 is mounted above each bearing 6 so as to extend vertically therefrom and each rod 7 carries a pair of nuts 8, 9. A support plate 10 having an aperture at each end thereof is located between the pairs of nuts 8, 9 and also extends between the threaded rods 7. A magnet 11 having a U-shaped transverse cross-section and a longitudinal extend slightly greater than the transverse width of the belt 1, depends from the support plate 10 and is thereby located over the belt 1 and drum 4.

The drum 4 is arranged to provide a stable base for the conveyor belt 1 so that the belt does not flap or move vertically in the vicinity of the magnet 11.

It is apparent that by manipulation of the nuts 8, 9 the magnet 11 can be raised and lowered relative to the belt 1. Thus as the belt 1 moves past the drum 4, the magnet 11 can be progressively lowered from a raised position (not illustrated) to a position closely adjacent the belt 1 as illustrated in FIGS. 1 and 2, thereby progressively destroying any spurious magnetic fields contained within the cords 2 and simultaneously permanently magnetizing the cords 2 longitudinally with a unidirectional magnetic field. Furthermore, once the desired degree of magnetization of the cords 2 has been achieved, the magnet 11 is slowly moved upwardly away from the belt 1 so as not to create any spurious magnetic field brought about by the rapid movement of the magnet 11.

Whilst the arrangement illustrated in FIGS. 1 and 2 is adequate for its intended purpose, the movement of the belt 1 over the idler roller 4 is not perfectly smooth because of the tendency of the belt 1 to flap or vibrate. In order to stabilize the belt an additional magnet 11A can be provided as illustrated in FIG. 3 upstream of the apparatus described in FIGS. 1 to 4 of the abovementioned Australian and U.S. patents, and which includes an input interface 16.

Thus the additional magnet 11A is employed below the belt 1 and located so as to provide a uniform field in the direction of the cords 2, that is the like poles of magnets 11 and 11A face each other ad both magnets 11 and 11A are mounted on to threaded rod with adjusting nuts in the same manner as magnet 11 of FIG. 1. This arrangement is of particular benefit in locations, for example of restricted space, where an idler roller 4 of FIGS. 1 and 2 cannot be made available to stabilize the belt.

In the arrangement of FIGS. 1 and 2 the magnet 11, and in FIG. 3 the magnets 11 and 11A, are permanent magnets and this is particularly advantageous in underground mines such as coal mines where inflammable gases may well be present. FIG. 4 illustrates an alternative to the magnets 11 and 11A of FIG. 3 in that electromagnets can be used. This has the advantage that the magnets 11 and 11A can remain stationary and the magnetic field thereof can be progressively increased by increasing the D.C. current supplied to the field windings.

As a consequence of the unidirectional magnetic field created within the cords 2, various substantially permanent magnetic fields are created as illustrated in FIG. 5. FIG. 5(a) illustrates the magnetic field for a break in the cord where the ends of the broken cord may be touching or abutting, possibly with a very small air gap. FIG. 5(b) illustrates the magnetic field for a gap in a cord where there is a substantial distance between the cord ends (for example 8 cm or 10 cm), and FIG. 5(c) illustrates the magnetic field created by a cord end such as may occur in spliced portions of the belt.

The belt is now moved past the apparatus described in FIGS. 1 to 4 of the abovementioned Australian and U.S. patents and re-produced in FIG. 3 with the field windings 6a and 6b energized with a 5 kHz signal which therefore induces a time varying magnetic field within the cords of the belt 1 in addition to the permanent unidirectional field already created therein.

Then the voltages which are induced in the sensing windings 7a and 7b of both yokes 2, 12 are added together in phase in order to produce the so called "corrosion signature" of the conveyor belt.

However, this corrosion signature is modified in as much as the data regarding corrosion of the cords is present in addition to the desired data concerning any breaks in the cords. In order to separate the corrosion data from the break data, it is necessary to filter the A+B signal produced by the sensing windings. Passing this combined signal through a high pass filter produces the corrosion data, however, passing the resultant signal through a low pass filter produces only the desired break data in the form of an electrical signal which as a function in the time provides an indication of the break condition of the cords.

The theoretical basis for this result may best be seen in relation to the graphs of FIG. 5 which are respectively a graph of the magnetic flux in the cord as a function of distance x along the cord corresponding to the cord conditions illustrated, and a graph as a function of time of the low frequency component of the voltage V of the output signal which is basically the negative differential of the flux distribution of the unidirectional magnetic field in accordance with Faraday's Law of Magnetic Induction.

It will therefore be apparent that from the voltage signal produced from the low pass filter, not only can a detection of breaks be made, but the type of the break (be it a (narrow) break, a gap, or a cord end), can be assessed and the location of the break in the belt can be determined from the timing of the voltage signal and knowledge of the speed and initial starting position of the belt.

In addition, the signal for the break data can also be used to discriminate between different types of splices. For example, the cord arrangements for a Type 1 and a Type 2 splice are respectively schematically illustrated in FIGS. 6 and 7. With the belt being treated as explained above and the output of the yokes 2,12 being amplified and passed through a low pass filter 20 the desired break data output voltage V illustrated in FIGS. 6 and 7 is obtained.

The resultant voltage V which is illustrated in solid lines in FIGS. 6 and 7 is made up from a number of component voltages each illustrated by a broken line and each derivable from the differential of the flux distribution of the corresponding cord of the cords forming the splice. It will be apparent that the graphs of FIGS. 6 and 7 provide an indication of the structural quality of their respective splices as well as an indication of the type of splice.

A belt containing a multiplicity of broken cords in a small region presents a low pass filtered output having a composite set of signals to a recorder (not illustrated). The richness of spikes in this output indicates many broken cords, whereas one glitch or spike is an indication of a single broken cord. A very large amplitude spike at one location on the belt indicates the existence of many broken cords at that location with the breaks being transversely aligned. Such a large amplitude spike therefore indicates a potential belt failure location.

Turning now to FIG. 8, there is schematically illustrated the cords of a conveyor belt having a number of cord defects listed as follows:
 A Corrosion including edge cord loss,
 B Corrosion of a single cord over a distance of approximately 10 cm,
 C A step increase of 1 cord at the termination of the edge cord loss,
 D A single broken cord,
 E Partial corrosion of a number of cords,
 F Two broken cords,
 G Few broken cords,
 H A Type 1 splice, and
 I A cord plane anomaly.

Following magnetic treatment of the belt as described above the belt is moved past the yokes 2,12 and the resultant output passed through a high pass filter 21 to obtain the conveyor belt corrosion signature V1 and through a low pass filter 20 to obtain the break data V2. The resultant traces for the items A to H above are illustrated.

For the item I, a voltage bump is recorded by the yodes 2,12 downstream from the pre-conditioning magnets 11,11A of FIG. 3 as cords which are not located in the centre plane of the belt pass the yokes 2,12.

These out of plane cords constitute an anomaly in which the cords in the belt at one transverse region of the belt are located closer to one belt surface than the other. This situation can arise either as an original manufacturing defect in the belt or as a result of relative vertical movement of the cords during use. The voltage bump results from the increased magnetisation of the cords as a result of the preconditioning of the displaced cord(s) in a higher magnetic field as it moves past one of the magnets 11,11A closer than they would have done had the cord(s) been located in the belt centre plane.

The foregoing describes only one embodiment of the present invention and modifications, obvious to those skilled in the art, can be made thereto without departing from the scope of the present invention. For example, the procedure can also be carried out using a single yoke thereby obtaining the conveyor belt signature to which is added the low frequency component brought about by the pre-arranged unidirectional magnetization of the belt cords.

A further useful modification is to provide two sets of yokes 2,12 each slightly more than half the belt width in length as schematically illustrated in FIG. 6 rather than a single set of yokes 2,12 having a length slightly greater than the belt width as illustrated in FIGS. 1, 7 and 8. With the two sets of yokes two sets of output signals are produced enabling each half of the belt to be monitored independently. This is advantageous with break detection since faults can then be located with increased transverse accuracy to either half of the belt width. Furthermore, in this arrangement a common mode signal VCM of the two resulting break traces VT (top voltage) and VB (bottom voltage) indicates any faults or breaks at the centre of the belt where the two sets of yokes overlap. Thus the belt is effectively longitudinally divided into 3 regions.

In addition, the magnetic pre-conditioning of the belt can use an AC magnetic field in order to reduce any stray magnetic flux contained within the cords, however, this de-gaussing procedure using AC fields may be undesirable depending on the frequency selected since it can result in recording of the AC frequency on the belt cords which provides a form of interference to the corrosion signature or conveyor belt signature monitoring which is normally done simultaneously with the break detection of the present invention. In addition, the interference frequencies may be low enough to pass through the low pass filters and appear on the break data.

What I claim is:
1. A method of detecting breaks in elongate magnetically permeable members embedded in a non-magnetically permeable material, said method comprising the steps of:
 (i) Substantially reducing or eliminating any stray or residual magnetic fields in said members by de-gaussing with an AC magnetic field prior to,
 (ii) Longitudinally magnetizing said members with a substantially unidirectional magnetic field thereby causing a fringing field at the location of an air gap at any breaks or breaks in said members,
 (iii) Causing relative movement between said material and a field winding means energized with a time varying electric current to induce a time varying longitudinally extending magnetic field in said members without also creating substantial eddy currents in said members,
 (iv) Causing relative movement between said material and a sensing winding means to generate an electrical signal in said sensing winding means indicative of a total magnetic field in said members while maintaining an orientation of said sensing winding means relative to said members to cause said sensing winding means to be subatantially insensitive to said eddy currents, and
 (v) passing said electric signal through a low pass filter to generate an output indicative of the location of said break or breaks.

2. A method as claimed in claim 1 wherein said electrical signal is passed through a high pass filter and said low pass filter simultaneously to generate a corrosion signature output (known per se) and said output indicative of the location of said break or breaks respectively, said two outputs being correlated in respect to time and thus longitudinal position of said members.

3. A method as claimed in claim 2 wherein said members comprise steel reinforcing cords in a conveyor belt.

4. A method as claimed in claim 3 wherein said field winding means and said sensing winding means are arranged in two sets, one of said sets extending transversely across one half of said conveyor belt and the other one of said sets extending transversely across the other half of said belt.

5. A method as claimed in claim 4 wherein a common mode signal is generated from each of the signals generated by the sensing winding means of each said set.

* * * * *